(12) United States Patent
Fujita

(10) Patent No.: US 11,224,406 B2
(45) Date of Patent: Jan. 18, 2022

(54) ULTRASOUND DIAGNOSIS APPARATUS AND ULTRASOUND PROBE MAINTENANCE APPARATUS

(71) Applicant: Toshiba Medical Systems Corporation, Otawara (JP)

(72) Inventor: Fuminori Fujita, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 382 days.

(21) Appl. No.: 15/450,222

(22) Filed: Mar. 6, 2017

(65) Prior Publication Data

US 2017/0290567 A1 Oct. 12, 2017

(30) Foreign Application Priority Data

Apr. 8, 2016 (JP) .............................. JP2016-077914

(51) Int. Cl.
*A61B 8/00* (2006.01)
*A61B 8/14* (2006.01)
*A61B 8/08* (2006.01)

(52) U.S. Cl.
CPC .............. *A61B 8/4444* (2013.01); *A61B 8/14* (2013.01); *A61B 8/461* (2013.01); *A61B 8/488* (2013.01); *A61B 8/5207* (2013.01); *A61B 8/54* (2013.01); *A61B 8/58* (2013.01)

(58) Field of Classification Search
CPC ... A61B 8/58–587; A61B 8/44; A61B 8/4444; A61B 8/14; A61B 8/461; A61B 8/488; A61B 8/5207; A61B 8/54; G01N 29/30; G01N 29/40; G01N 29/3363; G01N 29/44; G01N 29/48; G01S 7/5205; G01S 7/52004; G01S 7/52077
See application file for complete search history.

(56) References Cited

U.S. PATENT DOCUMENTS

| 5,517,994 A | 5/1996 | Burke et al. |
| 2007/0083111 A1* | 4/2007 | Hossack ................. A61B 8/12 600/437 |

(Continued)

FOREIGN PATENT DOCUMENTS

| JP | 8-238243 A | 9/1996 |
| JP | 2006-20749 A | 1/2006 |

(Continued)

OTHER PUBLICATIONS

Japanese Office Action dated Dec. 24, 2019 issued in Japanese Patent Application No. 2016-077914.

*Primary Examiner* — Christopher L Cook
(74) *Attorney, Agent, or Firm* — Oblon, McClelland, Maier & Neustadt, L.L.P.

(57) ABSTRACT

According to one embodiment, an ultrasound diagnosis apparatus includes a storage, a comparison function, and an evaluation function. The storage is provided in an ultrasound probe, and stores, in advance, an initial value of transmitting/receiving sensitivity measured with respect to each channel, of the ultrasound probe. The comparison function compares transmitting/receiving sensitivity newly measured with the initial value. The evaluation function evaluates the degree of the deterioration of the ultrasound probe based on a comparison result and a predetermined threshold value.

13 Claims, 10 Drawing Sheets

(56) References Cited

U.S. PATENT DOCUMENTS

| | | | |
|---|---|---|---|
| 2009/0299192 A1* | 12/2009 | Asafusa | B06B 1/0292 600/459 |
| 2010/0240992 A1* | 9/2010 | Hao | A61B 8/00 600/437 |
| 2012/0323514 A1* | 12/2012 | Nakazawa | G01B 17/00 702/65 |
| 2013/0194891 A1* | 8/2013 | Kristoffersen | A61B 8/58 367/13 |
| 2014/0024931 A1* | 1/2014 | Winston | A61B 5/0066 600/427 |
| 2014/0241115 A1* | 8/2014 | Thattari Kandiyil | G01S 7/52004 367/13 |
| 2017/0176581 A1* | 6/2017 | Ku | A61B 8/145 |
| 2018/0153517 A1* | 6/2018 | Chang | A61N 7/00 |

FOREIGN PATENT DOCUMENTS

| | | |
|---|---|---|
| JP | 2011-005023 A | 1/2011 |
| JP | 2011-050542 A | 3/2011 |

* cited by examiner

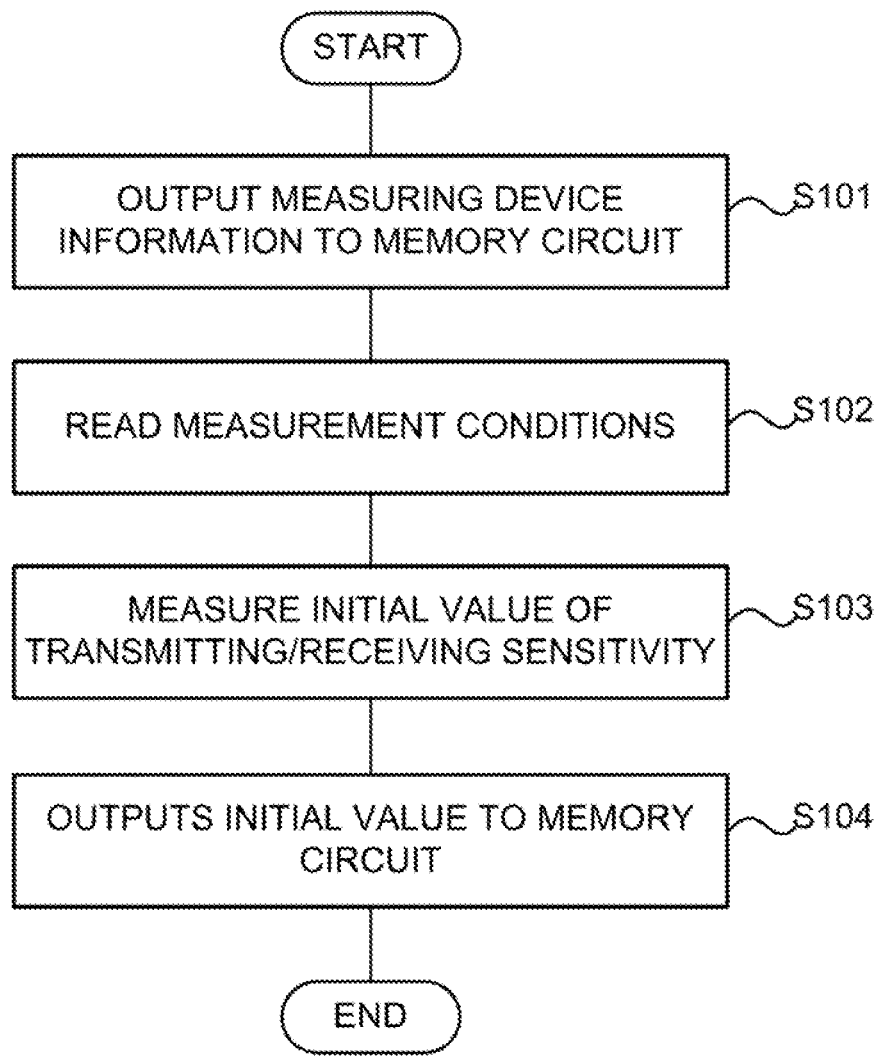

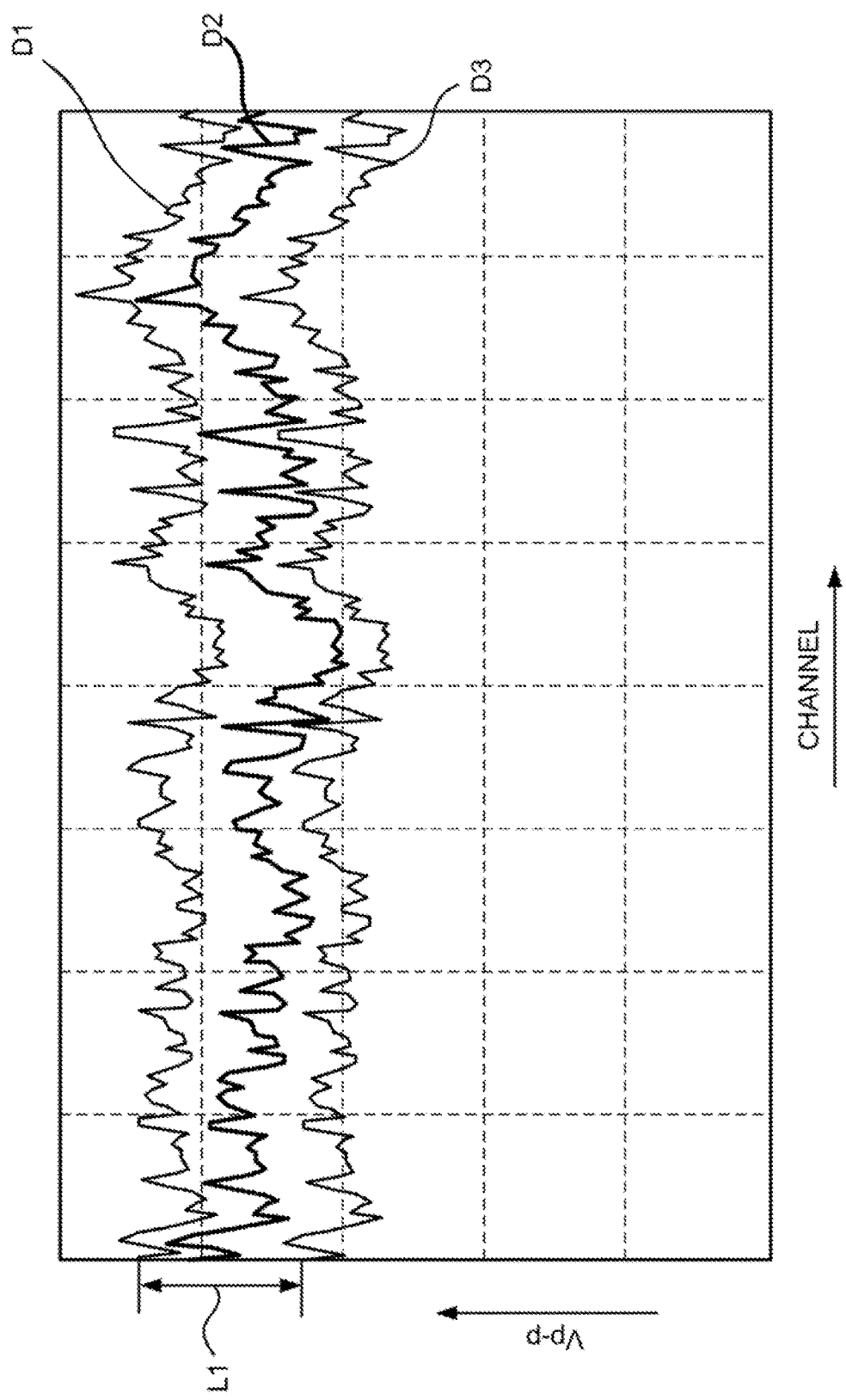

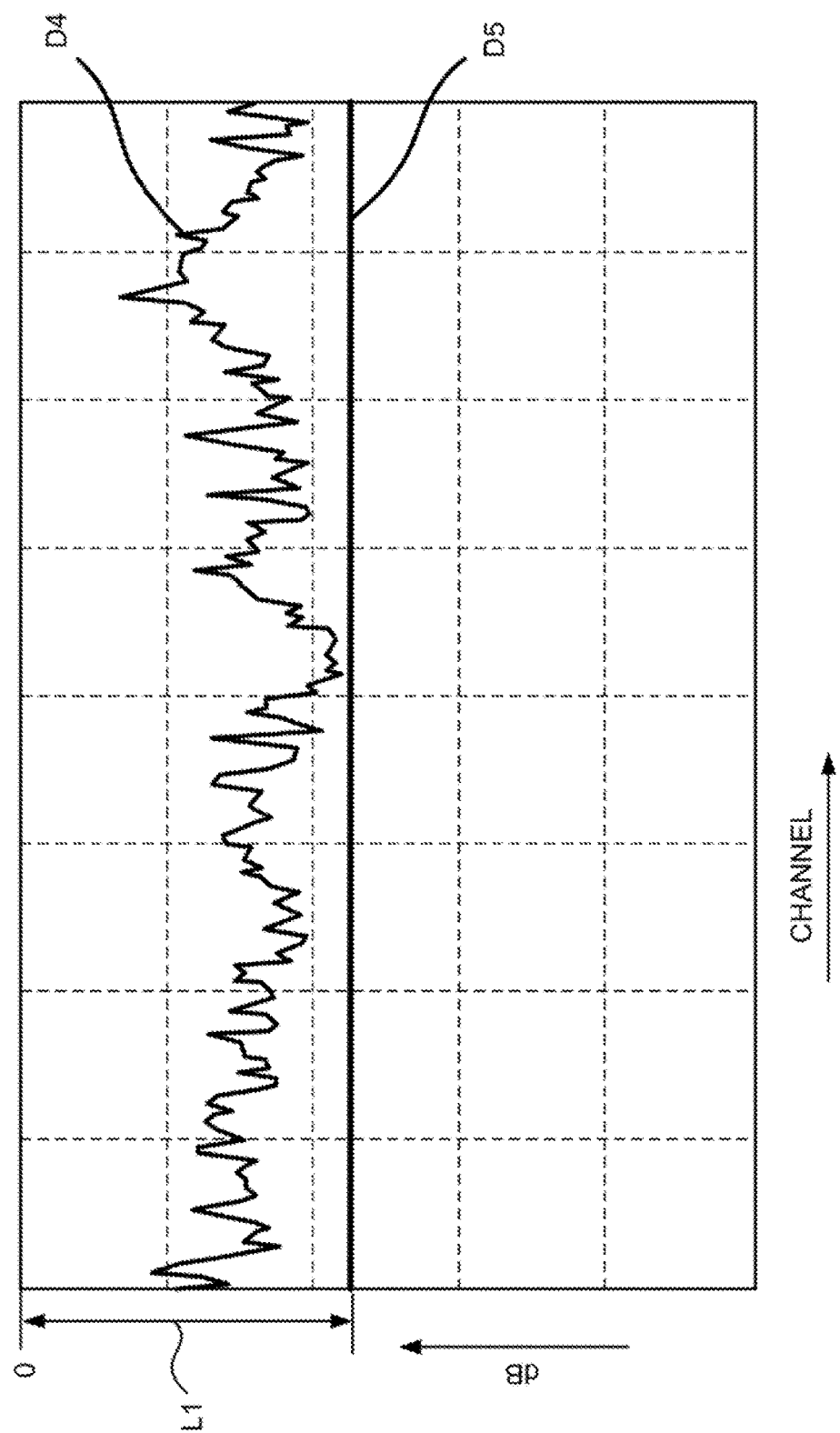

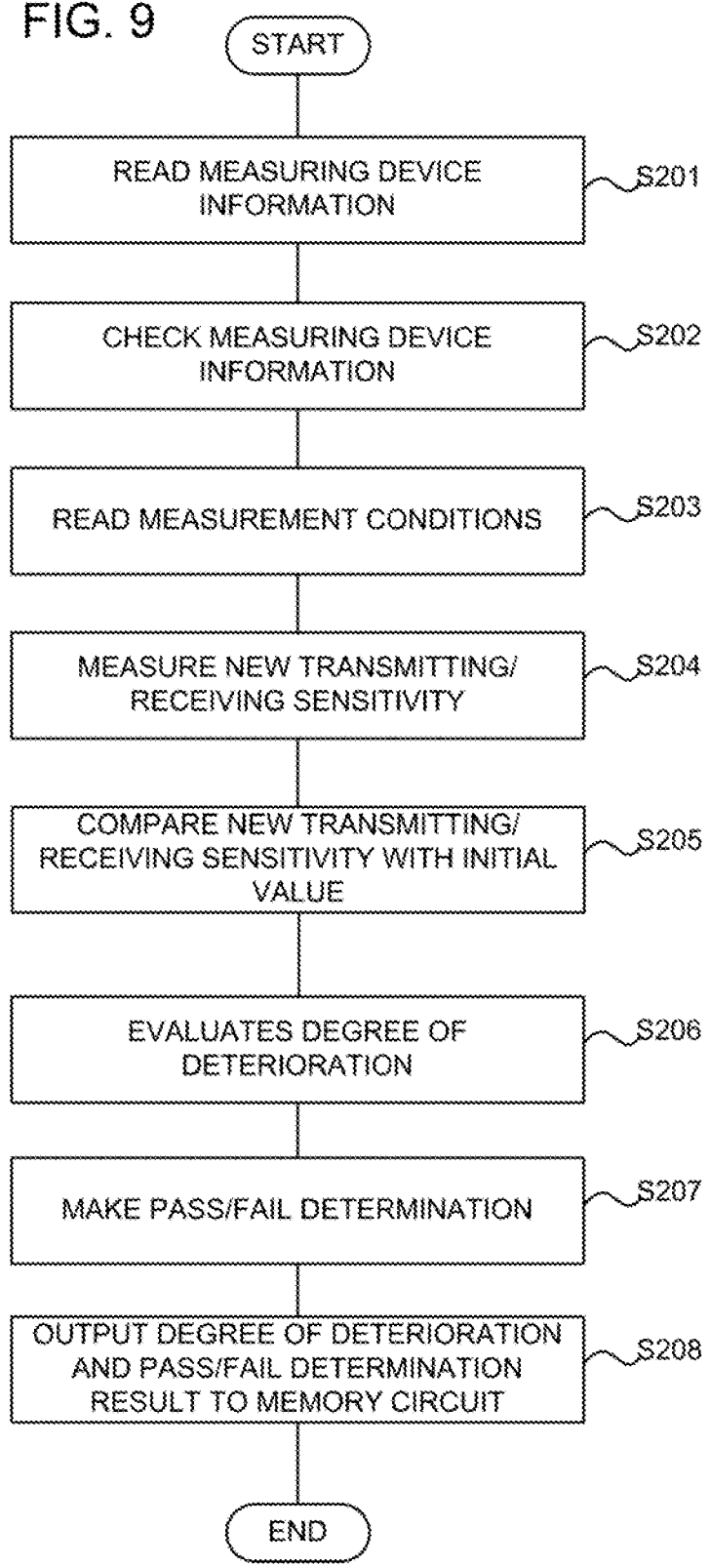

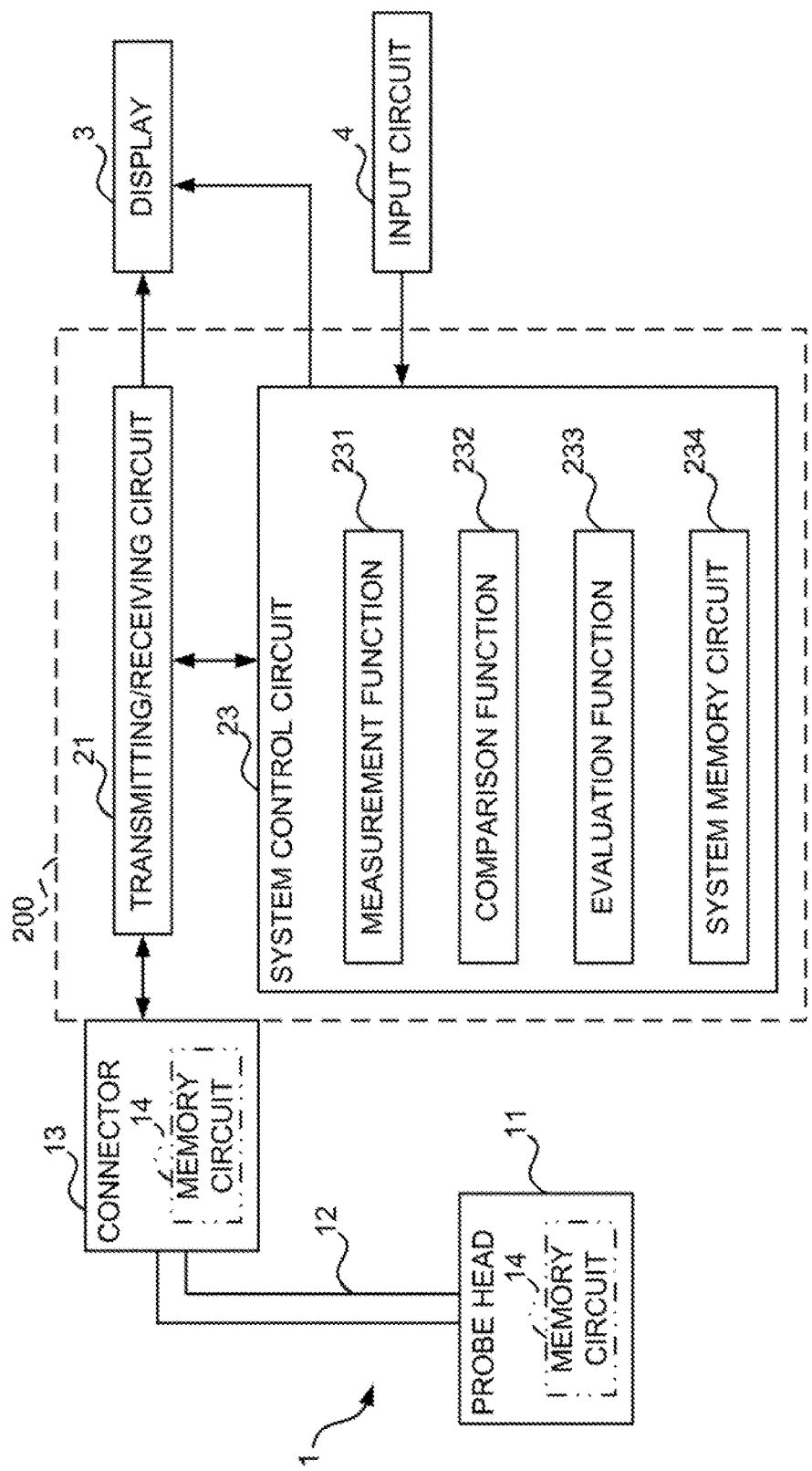

ULTRASOUND DIAGNOSIS APPARATUS AND ULTRASOUND PROBE MAINTENANCE APPARATUS

CROSS-REFERENCE TO RELATED APPLICATION

This application is based upon and claims the benefit of priority from Japanese Patent Application No. 2016-077914, filed Apr. 8, 2016; the entire contents all of which are incorporated herein by reference.

FIELD

Embodiments described herein relate generally to an ultrasound diagnosis apparatus and an ultrasound probe maintenance apparatus.

BACKGROUND

The ultrasound diagnosis apparatus transmits and receives ultrasound waves to and from a subject via an ultrasound probe having an ultrasound transducer, and generates an ultrasound image of the subject based on the received signal.

The sensitivity of the ultrasound probe deteriorates with use. It is presumed that this deterioration is caused by the change of the piezoelectric element and the electrode material of the ultrasound transducer with the passage of time due to energization as the ultrasound probe is repeatedly used. The deterioration of the sensitivity of the ultrasound probe may degrade the image quality of an ultrasound image to be generated.

Therefore, there have been proposed technologies for measuring the sensitivity of ultrasound probes. In one example of the technologies, the ultrasound transducer is driven while the acoustic lens of the ultrasound probe is left in the air, and the amplitude value of reflected wave reflected at the interface between the surface of the acoustic lens and the air is compared with a predetermined threshold value to thereby measure the sensitivity.

The measurement results of the sensitivity differ even among ultrasound probes of the same model. The difference is thought to be caused by variations in the manufacture of the ultrasound probe and use environments or conditions (e.g., driving time, etc.) after shipment. Therefore, if is desired to manage the sensitivity (initial value) of each ultrasound probe measured at the time of manufacture and compare it with the sensitivity of the same probe after shipment.

For this reason, according to the conventional technologies, each ultrasound probe is accompanied with a storage medium (e.g., CD-ROM, etc.) that stores the initial value of the sensitivity of the probe. Then, the sensitivity of the probe is measured after shipment, and compared with the initial value stored in the storage medium. The initial value of each ultrasound probe may be stored in a communication network such as the Internet, and, upon measuring the sensitivity of the probe after shipment, the initial value is retrieved and checked to compare it with the sensitivity.

BRIEF DESCRIPTION OF THE DRAWINGS

FIG. 6 is a flowchart illustrating the operation of the ultrasound diagnosis apparatus for measuring the initial value of the transmitting/receiving sensitivity according to the embodiment;

FIG. 7 is a schematic diagram illustrating transmitting/receiving sensitivity newly measured and the initial value according to the embodiment;

FIG. 8 is a schematic diagram illustrating a difference between the transmitting/receiving sensitivity newly measured and the initial value according to the embodiment;

FIG. 9 is a flowchart illustrating the operation of the ultrasound diagnosis apparatus for measuring the transmitting/receiving sensitivity at the time of maintenance checkup according to the embodiment; and p FIG. 10 is a block diagram illustrating a configuration of an ultrasound probe according to a modification.

DETAILED DESCRIPTION

Figure 1:
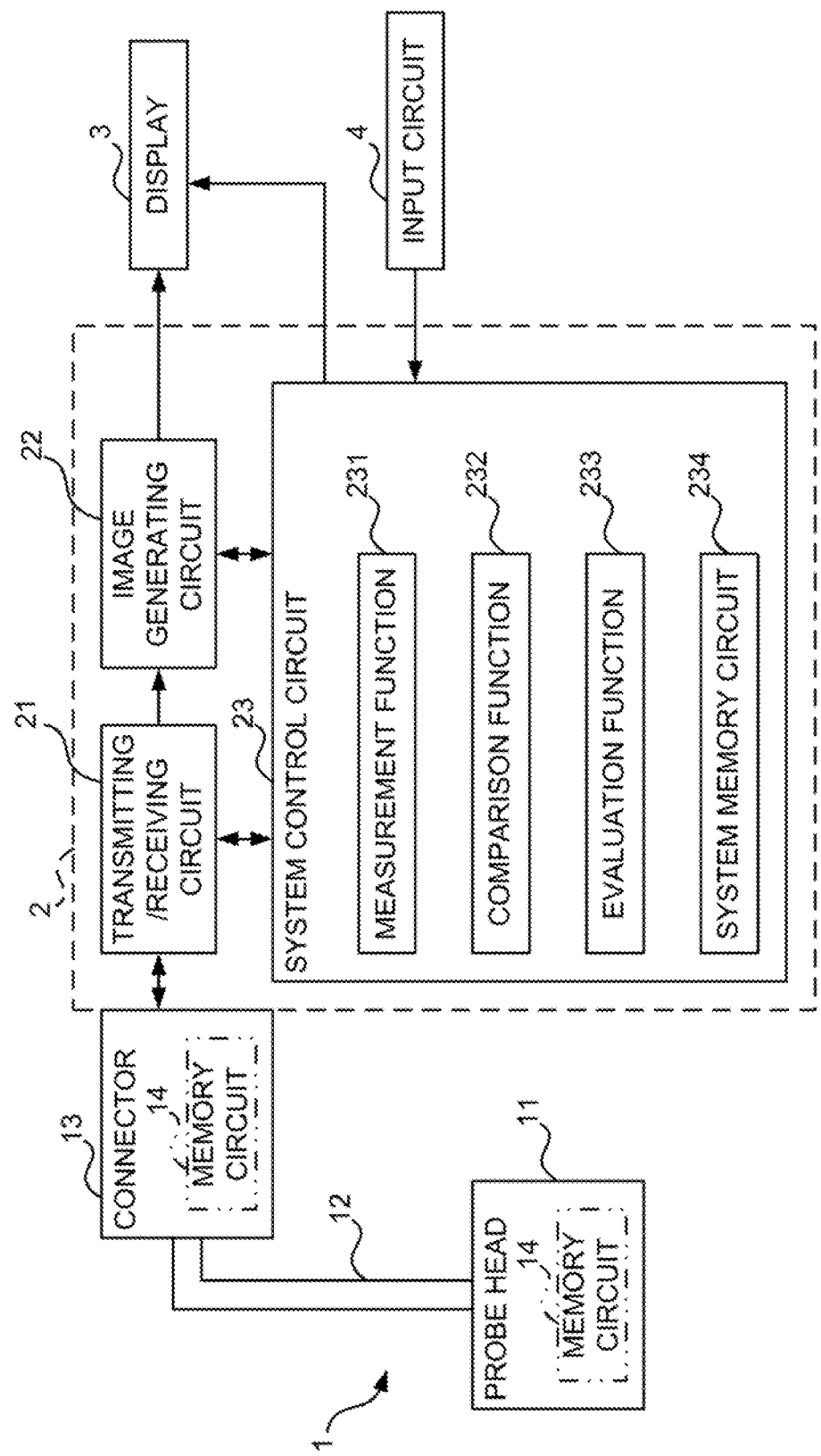
FIG. 1 is a block diagram illustrating a configuration of an ultrasound diagnosis apparatus according to an embodiment.

In general, according to one embodiment, an ultrasound diagnosis apparatus includes a storage, a comparison function, and an evaluation function. The storage is provided in an ultrasound probe, and stores, in advance, an initial value of transmitting/receiving sensitivity measured with respect to each channel of the ultrasound probe. The comparison function compares transmitting/receiving sensitivity newly measured with the initial value. The evaluation function evaluates the degree of the deterioration of the ultrasound probe based on a comparison result and a predetermined threshold value.

Referring now to the drawings, a description is given of an ultrasound diagnosis apparatus and an ultrasound probe maintenance apparatus according to embodiments.

EMBODIMENT

FIG. 1 is a block diagram illustrating a configuration of an ultrasound diagnosis apparatus according to an embodiment. The ultrasound diagnosis apparatus of the embodiment includes an ultrasound probe 1, a main unit 2, a display 3, and an input circuit 4.

Basic Configuration

The ultrasound probe 1 includes a probe head 11, a cable 12, a connector 13, and a memory circuit 14, Note that the memory circuit 14 may be mounted on either the probe head 11 or the connector 13. The memory circuit 14 of the embodiment is an example of a storage in the claims.

In the probe head 11, a plurality of ultra sound transducers vibrates based on a control signal from the main unit 2, thereby generating ultrasound waves. The ultrasound waves generated are transmitted to a subject. The ultrasound transducer receives reflected waves from the subject, and outputs an echo signal (RF signal) based on the received reflected wave to the ultrasound diagnosis apparatus.

The cable 12 and the connector 13 electrically connect the probe head 11 and the main unit 2. The control signal from the main unit 2 is sent to the probe head 11 via the connector 13 and the cable 12. Received signals are sent from the probe head 11 to the main unit 2 via the cable 12 and the connector 13.

The main unit 2 includes a transmitting/receiving circuit 21, an image generating circuit 22, and a system control circuit 23. The transmitting/receiving circuit 21 is a processor that outputs a pulse signal to the probe head 11 to generate ultrasound waves. The transmitting/receiving circuit 21 includes a pulser for each channel corresponding to each of the ultrasound transducers, and outputs a pulse signal for each channel. In addition, the transmitting/receiving circuit 21 receives an echo signal from each of the ultrasound transducers of the probe head 11. The transmitting/receiving circuit 21 amplifies echo signals from the probe head 11 with respect to each channel based on a set gain, and outputs the echo signals to the image generating circuit 22.

The image generating circuit 22 is a processor that generates ultrasound image data based on the echo signals from the transmitting/receiving circuit 21. For example, the image generating circuit 22 generates B-mode image data representing an image of tissue of the subject and Doppler image data representing blood flow information of the subject, and outputs the data to the display 3.

The system control circuit 23 is a processor that implements the functions of each circuit of the ultrasound diagnosis apparatus. In this embodiment, constituent elements, processing functions (described in detail later) performed by a measurement function 231, a comparison function 232, and an evaluation function 233 are stored in a system memory circuit 234 in the form of computer executable programs. The system control circuit 23 reads each of the programs from the system memory circuit 234 and executes it to realize a function corresponding to the program. In other words, having read the programs, the system control circuit 23 has the functions illustrated in FIG. 1. With reference to FIG. 1, the processing functions performed by the measurement function 231, the comparison function 232, and the evaluation function 233 are described as being realized by a single processing circuit; however, the functions may be realized fey a processing circuit formed of a plurality of independent processors that execute the programs.

The display 3 displays an ultrasound image based on the ultrasound image data from the image generating circuit 22. The display 3 is formed of a display device such as a liquid crystal display (LCD) or an organic electro-luminescence (EL) display. The display 3 of the embodiment is an example of a display in the claims.

The input circuit 4 receives operation by an operator such as a doctor, a technician, a service man for maintenance of the apparatus, or the like, and outputs a signal corresponding to the content of the operation to the system control circuit 23. For example, the input circuit 4 includes a trackball, a switch, button, a mouse, a keyboard, a touch command screen, a sensitivity time control (STC) slide volume, and the like.

The term "processor" as used herein refers to a circuit such as, for example, a central processing unit (CPU), a graphics processing unit (GPU), an application specific integrated, circuit (ASIC), a programmable logic device including a simple programmable logic device (SPLD) and a complex programmable logic device (CPLD), a field programmable gate array (FPGA), or the like. The processor reads programs out of the memory circuit and executes them to thereby realize the functions. The programs need not necessarily be stored in the memory circuit, the programs may be directly incorporated in the circuit of the processor. In this case, the processor realizes the functions by reading and executing the programs incorporated in the circuit. Each processor of the embodiment need not necessarily be configured as a single circuit. A plurality of independent circuits may be combined to form a single processor for implementing the functions. Besides, a plurality of constituent elements in FIG. 1 may be integrated into one processor to realize the functions.

The measurement function 231 of the embodiment is an example of the measuring in the claims. The comparison function 232 of the embodiment is an example of the comparison in the claims. The evaluation function 233 of the embodiment is an example of the evaluation in the claims.

Measurement of Transmitting/Receiving Sensitivity: Initial Value

First, a description is given of the measurement of the initial value of the transmitting/receiving sensitivity of the ultrasound probe 1. The memory circuit 14 stores, in advance, measurement conditions, i.e., conditions for measuring transmitting/receiving sensitivity for each channel of the ultrasound probe 1.

The measurement conditions are predetermined for each model of the ultrasound probe 1 and are input to the memory circuit 14. The measurement conditions include at least one of, for example, probe ID, drive voltage, drive frequency, gain, the number of channels, drive time, probe noise data (that is caused by the structure of the ultrasound probe 1, and varies depending on the ultrasound probe 1), and a variation correction value (described later) for each transmitting/receiving board. The variation correction value for each transmitting/receiving board is a value set according to the output characteristics of the transmitting/receiving circuit 21 or the like of the main unit 2.

The initial value of the transmitting/receiving sensitivity is generally measured during a period after the manufacture of the ultrasound probe 1 until the shipment thereof. When the connector 13 has been connected to the main unit 2, the system control circuit 23 measures the initial value of the transmitting/receiving sensitivity (the measurement function 231). At this time, the system control circuit 23 outputs measuring device information that can identify the main unit 2 as a measuring device to the memory circuit 14 to store the information. Thereby, information on the measuring device that has measured the initial value is stored in the memory circuit 14 in the ultrasound probe 1.

Then, the system control circuit 23 reads the measurement conditions from the memory circuit 14. The system control circuit 23 controls the transmitting/receiving circuit 21 based on the measurement conditions to drive the ultrasound probe. For example, the system control circuit 23 generates ultrasound waves in each of the ultrasound transducers based on the drive voltage, the drive frequency, the gain, the number of channels, the drive time, and the variation correction value for each transmitting/receiving board. Then, surface reflected waves are received from the ultrasound probe 1.

Figure 2:
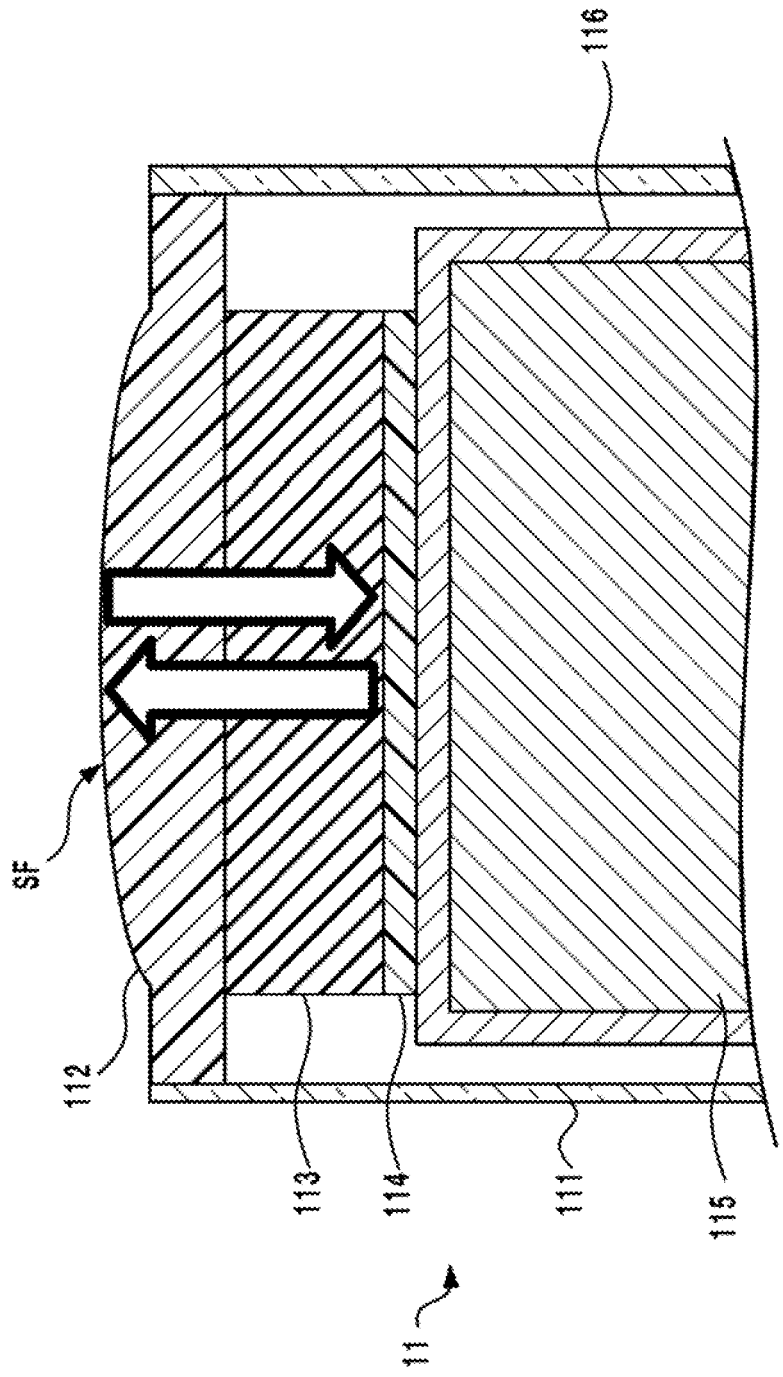
FIG. 2 is a schematic cross-sectional view of a probe head according to the embodiment.

FIG. 2 is a schematic cross-sectional view of the probe head 11 according to the embodiment. FIG. 2 illustrates, as an example, a cross section parallel to the arrangement direction of the ultrasound transducers (the lateral direction in FIG. 2). An acoustic lens 112 is arranged outside a housing 111 of the probe head. An acoustic matching layer 113 is provided in the housing 111 on the side close to the acoustic lens 112 (the distal end side of the probe head 11).

An ultrasound transducer group 114 is provided on the opposite side of the acoustic lens 112 in the acoustic matching layer 113. On the base end side of the ultrasound transducer group 114, a wiring board 116 and a backing material 115 are provided.

The system control circuit 23 controls the transmitting/receiving circuit 21 to cause each of the ultrasound transducers to generate ultrasound waves. The generated ultrasound waves are reflected at the interface SP between the surface of the acoustic lens 112 and the air. The reflected ultra so and waves (reflected waves) reach the ultrasound transducer group 114 and are received. Each of the ultrasound transducers outputs a signal (RF signal) including the reflected waves to the transmitting/receiving circuit 21.

Figure 3:
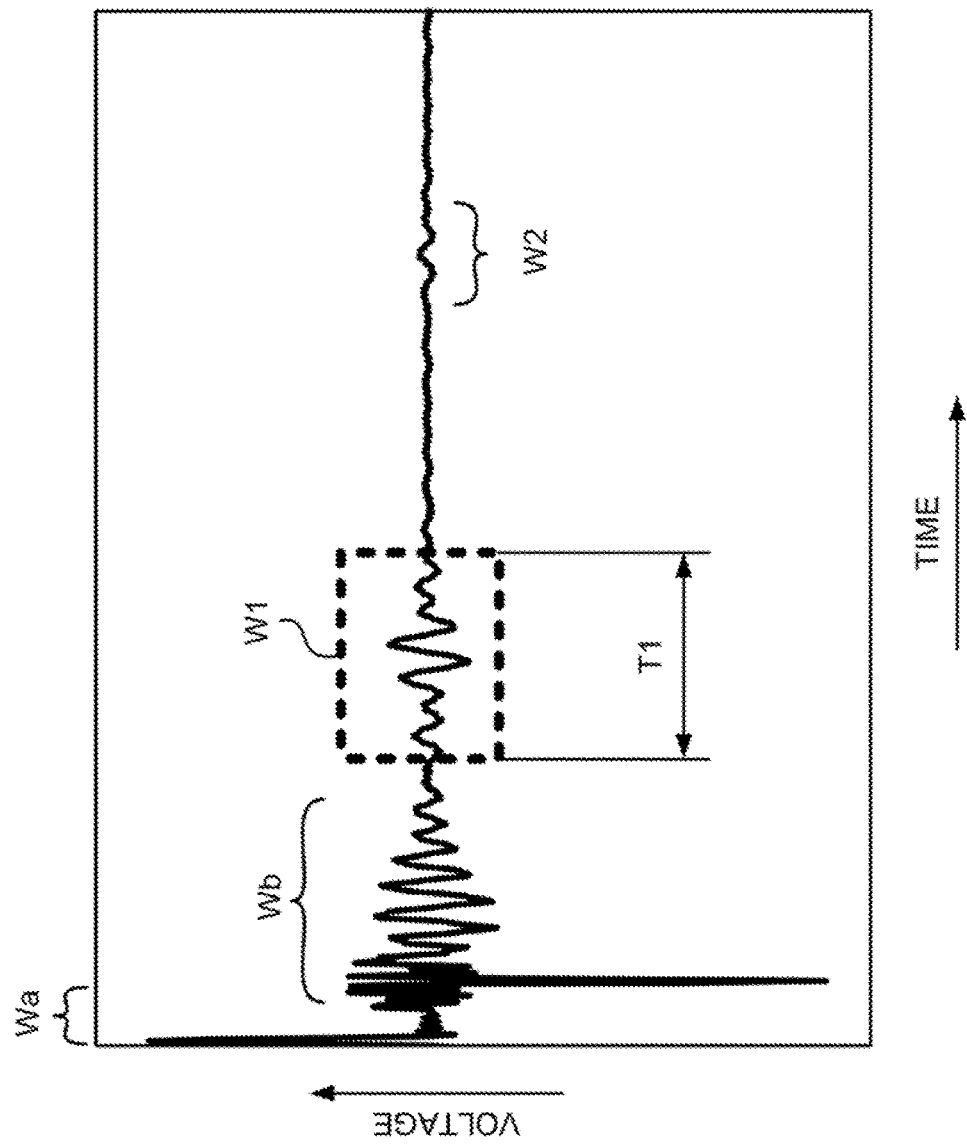
FIG. 3 is a schematic diagram illustrating an RF signal according to the embodiment.

The system control circuit 23 receives RF signals from the transmitting/receiving circuit 21. FIG. 3 is a schematic diagram illustrating an RF signal of the embodiment. The RF signals are collected with respect to each channel. The RF signal includes a transmission waveform Wa, multiple reflections and unnecessary vibration waveform Wb, a first reflected wave W1 that represents a first reciprocating reflected wave, i.e., first ultrasound wave that has reciprocated between the ultrasound transducer and the interface SF, and a second reflected wave W2 that represents a second reciprocating reflected wave, i.e., second ultrasound wave that has reciprocated between the ultrasound transducer and the interface SF. The first reflected wave W1 or the second reflected wave W2 is used as the surface reflected wave for measuring the transmitting/receiving sensitivity. Which one of the first reflected wave W1 and the second reflected wave W2 to use is determined in advance for each model of the ultrasound probe 1, In the following, an example is described in which the first reflected wave W1 is used.

For example, the system control circuit 23 specifies the first reflected wave W1 based on a time range T1 determined in advance for each model of the ultrasound probe. The time range T1 is stored in advance in the memory circuit 14. The system control, circuit 23 extracts; a signal in the time range T1 in the RF signal, and thereby identifies the first reflected wave W1.

For another example, the system control circuit 23 may subtract probe noise data from the RF signal to obtain the first reflected wave W1 (surface reflected wave). The probe noise data is data unique to the ultrasound probe, and indicates a waveform other than the surface reflected wave. The probe noise data is stored in the memory circuit 14, The system control circuit 23 can obtain the first reflected wave W1 by reading the probe noise data from the memory circuit 14 and subtracting the probe noise data from the RF signal.

Figure 4:
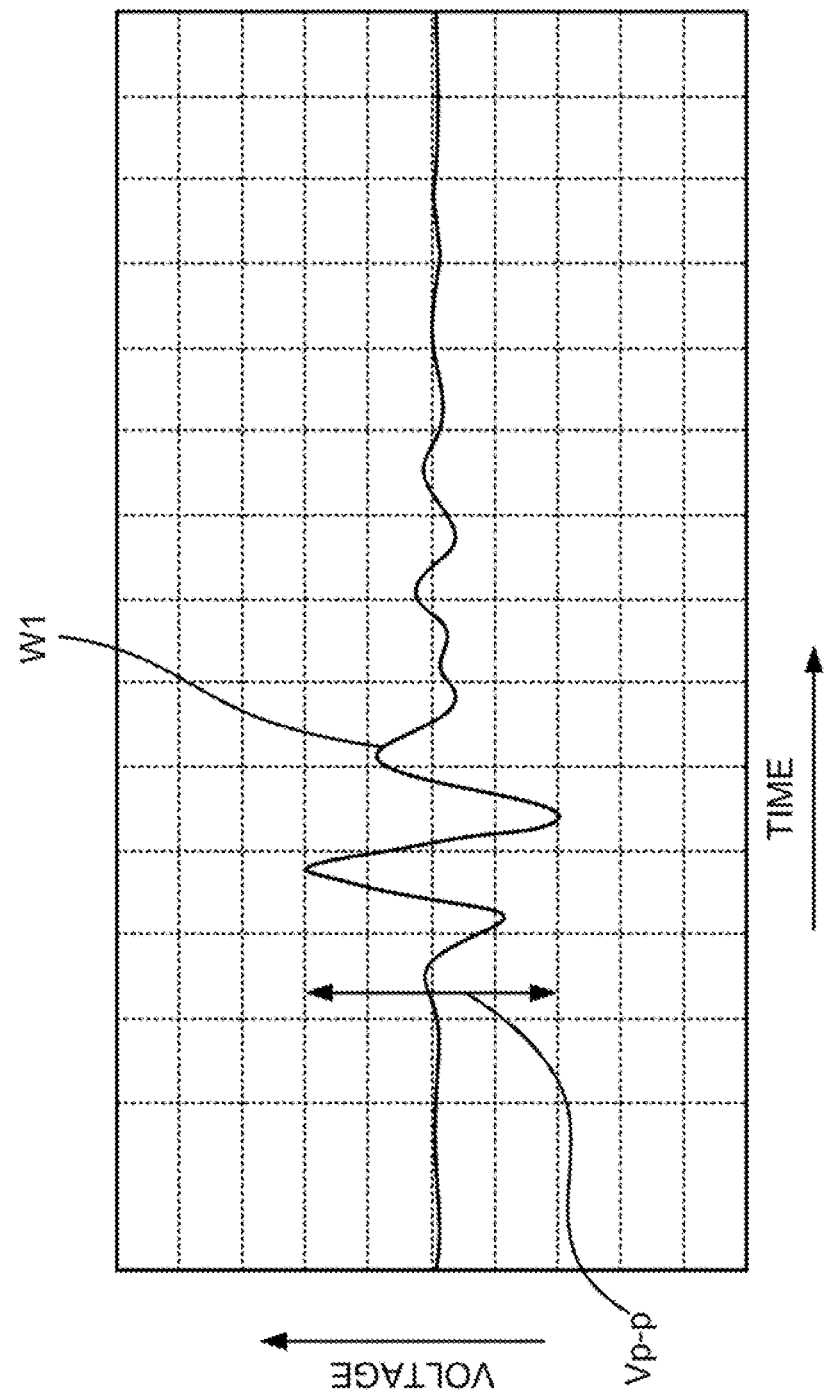
FIG. 4 is a schematic diagram illustrating a first reflected wave according to the embodiment.
Figure 5:
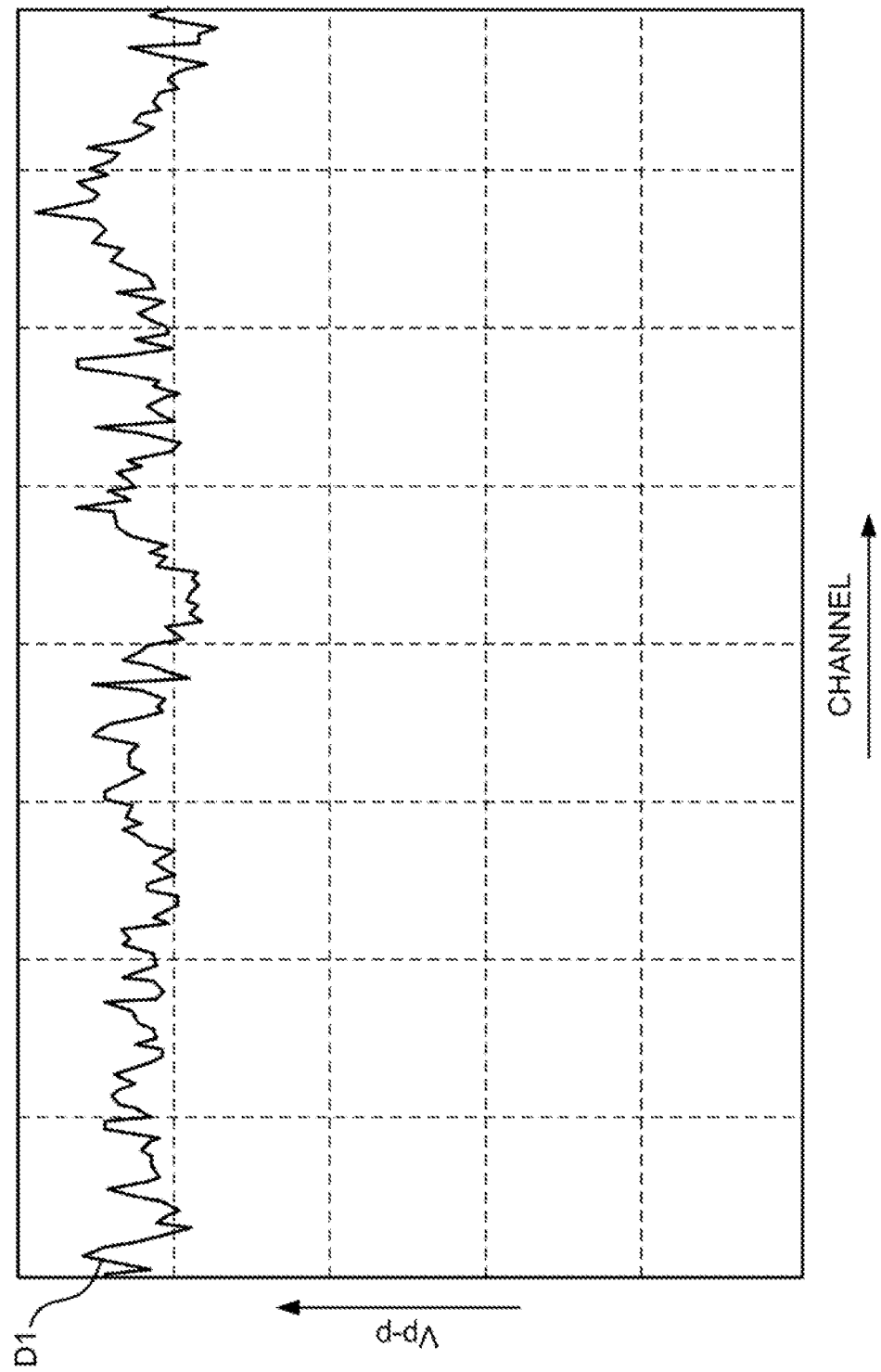
FIG. 5 is a schematic diagram illustrating transmitting/receiving sensitivity of each channel according to the embodiment.

FIG. 4 is a schematic diagram illustrating the first reflected wave of the embodiment. The system control circuit 23 obtains the amplitude value in the first reflected wave. In general, the maximum amplitude value (Vp–p) in the first reflected wave is obtained. The amplitude value obtained corresponds to the transmitting/receiving sensitivity in the relevant channel. The system control circuit 23 obtains the amplitude value as an initial value for each channel. Further, in the case of initial value measurement, the system control circuit 23 makes a pass/fail determination on the transmitting/receiving sensitivity based on a predetermined design value, and outputs data-indicating the initial value, the pass/fail determination result, and the measurement date and time to the memory circuit 14 to store the data. FIG. 5 is a schematic diagram illustrating the transmitting/receiving sensitivity for each channel according to the embodiment. An initial value D1 representing the transmitting/receiving sensitivity obtained for each channel is stored in the memory circuit 14.

FIG. 6 is a flowchart illustrating the operation of the ultrasound diagnosis apparatus for measuring the initial value of the transmitting/receiving sensitivity according to the embodiment.

Step S101: After the connector 13 of the ultrasound probe 1 is connected to the main unit 2, the system control circuit 23 outputs measuring device information that can identify the main unit 2 as a measuring device to the memory circuit 14 to stores the information.

Step S102: The system control circuit 23 reads the measurement conditions from the memory circuit 14. The measurement conditions are determined in advance with respect to each model of the ultrasound probe 1 and are stored in the memory circuit 14.

Step S103: The system control circuit 23 controls the transmitting/receiving circuit 21 to cause each of the ultrasound transducers to generate ultrasound waves. The system control circuit 23 receives an RF signal from the transmitting/receiving circuit 21 with respect to each channel. The system control circuit 23 obtains the surface reflected wave from the RF signal and obtains the transmitting/receiving sensitivity.

Step S104: In the case of initial value measurement, the system control circuit 23 makes a pass/fail determination on the transmitting/receiving sensitivity based on a predetermined design value, and outputs data indicating the initial value, the pass/fail determination result, and the measurement date and time to the memory circuit 14 to store the data.

The ultrasound probe 1 is used for various diagnoses as the memory circuit 14 thereof stores the initial value of the transmuting receiving sensitivity thus measured.

Transmitting/Receiving Sensitivity Measurement: Management Measurement

Described below is management measurement for checking the deterioration of the transmitting/receiving sensitivity of the ultrasound probe 1. The management measurement is performed, for example, during maintenance checkup by an operator such as a service person (manual measurement). In addition, the management measurement may be automatically performed each time the ultrasound probe 1 is connected to the main unit 2 after a predetermined period of time has elapsed (automatic measurement). In the following, manual measurement is described.

Upon receipt of an operation by the operator, the system control circuit 23 reads, from the memory circuit 14, measuring device information indicating a measuring device in which the initial value has been measured. The system control circuit 23 compares the measuring device information indicating a measuring device in which the initial value has been measured with the measuring device information of the main unit 2 to which the ultrasound probe 1 is connected at the time of maintenance checkup, and determines whether the measurement, conditions need to be corrected. A common technique can be used for this determination. For example, the system control circuit 23 determines whether to correct the measurement conditions according to the output characteristics of the transmitting/receiving circuit 21 of the main unit 2. Then, the system control circuit 23 reads the measurement conditions from the memory circuit 14. The system control circuit 23 measures a new transmitting/ receiving sensitivity for each channel by the same processing as in the initial measurement of the transmitting/receiving sensitivity.

The system control circuit 23 reads the Initial value D1 from the memory circuit 14 and compares the transmitting/receiving sensitivity newly measured with the initial value (the comparison function 232). FIG. 7 is a schematic diagram illustrating the transmitting/receiving sensitivity D2 newly measured and the Initial value D1 of the embodiment. The transmitting/receiving sensitivity D2 newly measured at the time of maintenance checkup is usually deteriorated as compared to the initial value D1. The transmitting/receiving sensitivity deteriorates individually in each channel, and does not deteriorate uniformly in all channels. Therefore, the graph shape of the transmitting/receiving sensitivity D2 is different from that of the initial value D1. Further, a threshold line D3, which has decreased from the initial value D1 by a threshold value L1, is obtained by translating the graph shape of the initial value D1 by the threshold value L1, and its shape is the same as the graph shape of the initial value D1. The threshold value L1 is determined in advance for each model of the ultrasound probe and stored in the memory circuit 14.

The system control circuit 23 evaluates the degree of the deterioration of the ultrasound probe 1 based on the threshold value L1 determined in advance (the evaluation function 233). At this time, the system control circuit 23 reads the initial value D1 and the threshold value L1 from the memory circuit 14, and counts the number of channels in which the transmitting/receiving sensitivity D2 is below the threshold line D3. The number of channels counted corresponds to the degree of deterioration. The greater the number of channels where the transmitting/receiving sensitivity is below the threshold line D3, the more the transmitting/receiving sensitivity of the ultrasound probe 1 has deteriorated. FIG. 8 is a schematic diagram illustrating the difference D4 between the transmitting/receiving sensitivity D2 newly measured and the initial value D1 of the embodiment. Among the channels with the difference D4, the greater the number of channels where the difference D4 is below the threshold line D5, the more the transmit ting/receiving sensitivity of the ultrasound probe 1 has deteriorated.

When the degree of deterioration exceeds a predetermined value, the system control circuit 23 determines the transmitting/receiving sensitivity as "Fail" in the pass/fail determination. On the other hand, when the degree of deterioration is below the predetermined value, the system control circuit 23 determines the transmitting/receiving sensitivity as "Pass" in the pass/fail determination. The system control circuit 23 outputs the determination result to the display 3 to display it as an evaluation result. At this time, the system control circuit 23 may output the transmitting/receiving sensitivity D2 measured, the initial value D1, and the threshold line D3 to the display 3 to display them as the evaluation result. Thereby, the operator can know the degree of deterioration of the ultrasound probe 1 and the result of the pass/fail determination. Further, the degree of deterioration and the pass/fail determination result may be output to a general, printer so that they can be printed.

Such the pass/fail determination requires the initial value obtained on the first measurement date and the transmitting/receiving sensitivity obtained on the latest measurement date. Meanwhile, in order to grasp the transition of the temporal deterioration, data on the degree of deterioration may be accumulated and stored in every maintenance checkup. In this case, the system control circuit 23 outputs data indicating the transmitting/receiving sensitivity D2 measured, the pass/fail determination result, and the measurement date and time to the memory circuit 14 to store the data each time the transmitting/receiving sensitivity is measured and the pass/fail determination is made. As a result, the transition of the temporal deterioration of the ultrasound probe 1 is stored in the memory circuit 14 in the ultrasound probe 1.

FIG. 9 is a flowchart illustrating the operation of the ultrasound diagnosis apparatus for measuring the transmitting/receiving sensitivity at the time of maintenance checkup according to the embodiment.

Step S 201: The system control circuit 23 receives operation by the operator and reads, from the memory circuit 14, measuring device information indicating a measuring device that has measured the initial value D1.

Step S202: The system control circuit 23 checks the measuring device information indicating a measuring device that has measured the initial value D1 with the measuring device information of the main unit 2 to which the ultrasound probe 1 is connected at the time of maintenance checkup, and determines whether the measurement, conditions need to be corrected.

Step S 203: The system control circuit 23 reads measurement conditions from the memory circuit 14.

Step S204: The system control circuit 23 measures a new transmitting/receiving sensitivity D2 for each channel by the same processing as in the initial measurement of the transmitting/receiving sensitivity.

Step S205: The system control circuit 23 compares the transmitting/receiving sensitivity D2 newly measured with the initial value D1.

Step S206: The system control circuit 23 evaluates the degree of the deterioration of the ultrasound probe 1 based on the threshold value L1 determined in advance. At this time, the system control circuit 23 reads the initial value D1 and the threshold value L1 from the memory circuit 14, and counts the number of channels in which the transmitting/receiving sensitivity D2 newly measured is below the threshold fine D3.

Step S207: When the degree of deterioration exceeds a predetermined value, the system control circuit 23 determines the transmitting/receiving sensitivity as "fail" in the pass/fail determination. On the other hand, when the degree of deterioration is below the predetermined value, the system control circuit 23 determines the transmitting/receiving sensitivity as "Pass" in the pass/fail determination.

Step S208: The system control circuit 23 outputs data indicating the transmitting/receiving sensitivity D2 newly measured, the pass/fail determination result, and the measurement date and time to the memory circuit 14 to store the data.

According to this embodiment, it is possible to easily compare the initial value of the transmitting/receiving sensitivity and the Latest transmitting/receiving sensitivity of the same ultrasound probe. Thus, the accuracy of the evaluation of the degree of deterioration as well as the pass/fail determination is improved. In addition, since the initial value of the transmitting/receiving sensitivity and the measurement conditions are stored in the memory circuit in the ultrasound probe, it is possible to prevent such a situation in which the storage medium is lost and the initial value of the ultrasound probe becomes unknown. Further, even when the ultrasound probe is connected to different main units at the time of shipment and maintenance checkup, the initial value of the transmitting/receiving sensitivity and the measurement conditions can be read out from the memory circuit in the ultrasound probe. This enables easy maintenance checkup and the correction of variations in devices.

Modification

FIG. 10 is a block diagram illustrating a configuration of a maintenance apparatus 200 for an ultrasound probe according to a modification. The maintenance apparatus 200 is a measurement dedicated device used mainly for measurement of an ultrasound probe at the time of shipment and maintenance checkup, and is different from the ultrasound diagnosis apparatus in that it does not have the ultrasound image generating function. Otherwise, the maintenance apparatus 200 has the same configuration as that of the ultrasound diagnosis apparatus described above. Also with the maintenance apparatus 200 of this modification, it is possible to easily compare the initial value of the transmitting/receiving sensitivity and the latest transmitting/receiving sensitivity of the same ultrasound probe. Thus, the accuracy of the evaluation of the degree of deterioration as well as the pass/fail determination is improved.

According to the ultrasound diagnosis apparatus and the ultrasound probe maintenance apparatus of at least one embodiment described above, it is possible to easily compare the initial value and a measured value of the transmitting/receiving sensitivity of the ultrasound probe.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus, comprising:
a main apparatus including processing circuitry; and
an ultrasound probe connected to the main apparatus and including a storage;
wherein
the storage is configured to store an initial value of transmitting/receiving sensitivity measured in advance with respect to each channel of the ultrasound probe, measuring-device information, and measurement conditions having been used to measure the initial value of the transmitting/receiving sensitivity, the measuring-device information being for allowing identification of a measuring device having measured the initial value, the measurement conditions being for measuring the transmitting/receiving sensitivity with respect to each channel of the ultrasound probe for the purpose of evaluating a degree of deterioration of the ultrasound probe; and
the processing circuitry is configured to:
read the stored measurement conditions from the storage;
newly measure transmitting/receiving sensitivity based on the measurement conditions that have been used to measure the initial value of the transmitting/receiving sensitivity;
compare the initial value with the newly measured transmitting/receiving sensitivity;
evaluate the degree of deterioration of the ultrasound probe based on a predetermined threshold value and a result of the comparison of the initial value and the newly measured transmitting/receiving sensitivity;
read the stored measuring-device information from the storage;
compare the read measuring-device information and measuring-device information of the main apparatus connected to the ultrasound probe at a time of a maintenance checkup; and
determine from a result of the comparison whether to correct the measurement conditions.

2. The ultrasound diagnosis apparatus of claim 1, wherein the transmitting/receiving sensitivity includes a radio frequency (RF) signal and an amplitude value with respect to each channel of the ultrasound probe.

3. The ultrasound diagnosis apparatus of claim 1, wherein the predetermined threshold value is determined in advance for each model of the ultrasound probe.

4. The ultrasound diagnosis apparatus of claim 1, wherein the measurement conditions include at least one of drive voltage, drive frequency, gain, number of channels, drive time, probe noise data, and a variation correction value for each transmitting/receiving board.

5. The ultrasound diagnosis apparatus of claim 4, wherein the processing circuitry is further configured to subtract the probe noise data from an RF signal of the ultrasound probe to obtain surface reflected wave of the ultrasound probe, and obtain at least one of the initial value and the newly measured transmitting/receiving sensitivity based on the surface reflected wave.

6. The ultrasound diagnosis apparatus of claim 1, further comprising a display configured to display the result of the comparison.

7. The ultrasound diagnosis apparatus of claim 1, wherein the processing circuitry is further configured to:
determine whether the number of channels having the transmitting/receiving sensitivity of below a threshold value exceeds a predefined value, and
determine a pass or a fail for the transmitting/receiving sensitivity on a basis of a result of the channel-number determination.

8. The ultrasound diagnosis apparatus of claim 1, comprising wherein
the processing circuitry is further configured to:
automatically perform management measurement of the transmitting/receiving sensitivity of the ultrasound probe at certain time intervals to check deterioration of the ultrasound probe,
read the stored measurement conditions from the storage at the time of performing the management measurement,
newly measure transmitting/receiving sensitivity based on the measurement conditions that have been used to measure the initial value of the transmitting/receiving sensitivity,
compare the initial value with the newly measured transmitting/receiving sensitivity, and
evaluate a degree of deterioration of the ultrasound probe based on a predetermined threshold value and a result of the comparison of the initial value and the newly measured transmitting/receiving sensitivity.

9. The ultrasound probe maintenance apparatus of claim 1, wherein
the processing circuitry is further configured to:
measure the transmitting/receiving sensitivity for evaluating the degree of deterioration and the initial value of the transmitting/receiving sensitivity, and for measuring the initial value, cause a result of pass/fail determination to be stored in the storage.

10. An ultrasound probe maintenance apparatus, comprising:

an ultrasound probe; and processing circuitry configured to:

read an initial value of transmitting/receiving sensitivity measured with respect to each channel of the ultrasound probe from a storage of the ultrasound probe;

read measurement conditions having been used to measure the initial value of the transmitting/receiving sensitivity from the storage, the measurement conditions being for measuring the transmitting/receiving sensitivity with respect to each channel of the ultrasound probe for the purpose of evaluating a degree of deterioration of the ultrasound probe;

newly measure transmitting/receiving sensitivity based on the measurement conditions that have been used to measure the initial value of the transmitting/receiving sensitivity;

compare the initial value with the newly measured transmitting/receiving sensitivity;

evaluate a degree of deterioration of the ultrasound probe based on a predetermined threshold value and a result of the comparison of the initial value and the newly measured transmitting/receiving sensitivity;

read measuring-device information from the storage of the ultrasound probe, the measuring-device information being for allowing identification of a measuring device having measured the initial value;

compare the read measuring-device information and measuring-device information of a main apparatus connected to the ultrasound probe at a time of a maintenance checkup; and determine from a result of the comparison whether to correct the measurement conditions.

11. The ultrasound probe maintenance apparatus of claim 10, wherein

The processing circuitry is further configured to:

determine whether the number of channels having the transmitting/receiving sensitivity of below a threshold value exceeds a predefined value, and determine a pass or a fail for the transmitting/receiving sensitivity on a basis of a result of the channel-number determination.

12. The ultrasound probe maintenance apparatus of claim 10, wherein the processing circuitry is further configured to:

automatically perform management measurement of transmitting/receiving sensitivity of the ultrasound probe at certain time intervals to check deterioration of the ultrasound probe, read an initial value of transmitting/receiving sensitivity measured with respect to each channel of the ultrasound probe from a storage of the ultrasound probe at the time of performing the management measurement, read measurement conditions having been used to measure the initial value of the transmitting/receiving sensitivity from the storage, the measurement conditions being for measuring the transmitting/receiving sensitivity with respect to each channel of the ultrasound probe, newly measure transmitting/receiving sensitivity based on the measurement conditions that have been used to measure the initial value of the transmitting/receiving sensitivity, compare the initial value with the newly measured transmitting/receiving sensitivity, and evaluate a degree of deterioration of the ultrasound probe based on a predetermined threshold value and a result of the comparison of the initial value and the newly measured transmitting/receiving sensitivity.

13. The ultrasound probe maintenance apparatus of claim 10, wherein the processing circuitry is further configured to:

measure the transmitting/receiving sensitivity for evaluating the degree of deterioration and the initial value of the transmitting/receiving sensitivity, and for measuring the initial value, cause a result of pass/fail determination to be stored in the storage.

* * * * *